United States Patent [19]

Leung

[11] Patent Number: 5,374,549
[45] Date of Patent: Dec. 20, 1994

[54] PROCESS OF ENRICHING ADHERENT CD4+ T CELLS FROM MONOCYTE DEPLETED PERIPHERAL BLOOD MONONUCLEAR CELLS WITH INTERLEUKIN 2 AND INTERLEUKIN 4

[75] Inventor: Kam H. Leung, Brookhaven, Pa.

[73] Assignee: Terumo Corporation, Tokyo, Japan

[21] Appl. No.: 648,672

[22] Filed: Jan. 31, 1991

[51] Int. Cl.⁵ .................... C12N 5/00; A61K 45/05
[52] U.S. Cl. .................... 435/240.2; 435/240.21; 435/240.23; 424/85.2
[58] Field of Search ........... 435/240.2, 240.23, 240.26, 435/240.27, 240.21; 424/529, 577, 85.2

[56] References Cited

U.S. PATENT DOCUMENTS

| | | | |
|---|---|---|---|
| 4,849,329 | 7/1989 | Leung et al. | 435/2 |
| 5,108,760 | 7/1989 | Irr et al. | 424/534 |
| 5,126,132 | 6/1992 | Rosenberg | 424/93 |

OTHER PUBLICATIONS

Melder et al, Cancer Research, 48, pp. 3461–3469 (Jun. 15, 1988).
Hoyer et al, Cancer Research, 46 (1986) pp. 2834–2838.
Kawakami et al, J. of Immunology vol. 142, No. 10, May 1989, pp. 3452–3461.
Reinhold et al, J. Invest. Dermatol 96 (3). 1991, pp. 370–375.

*Primary Examiner*—Douglas W. Robinson
*Assistant Examiner*—Susan M. Dadio
*Attorney, Agent, or Firm*—Burns, Doane, Swecker & Mathis

[57] ABSTRACT

Peripheral blood mononuclear cells (PBMC) are treated to deplete monocytes and the remaining cells are cultured in a medium containing interleukin-2 (IL-2) and interleukin-4 (IL-4). Nonadherent cells are removed and discarded, and adherent cells are further cultured in a medium of IL-2 and IL-4 which expands the CD4+ T cells population of the PBMC. The expanded, enriched CD4+T cells can be placed in a pharmaceutically acceptable carrier and administered to a mammal with IL-2 to treat a tumor.

11 Claims, No Drawings

PROCESS OF ENRICHING ADHERENT CD4+ T CELLS FROM MONOCYTE DEPLETED PERIPHERAL BLOOD MONONUCLEAR CELLS WITH INTERLEUKIN 2 AND INTERLEUKIN 4

CROSS-REFERENCE

The following application, filed concurrently herewith, is incorporated herein by reference: Kam H. Leung, "Enhanced Generation of Adherent Lymphokine-activated Killer Cells with Interleukin-2 and Interleukin-4 from L-phenylalanine Methyl Ester-treated Human Peripheral Blood Cells", Ser. No. 07/648,676, filed Jan. 31, 1991, now abandoned.

BACKGROUND OF THE INVENTION

Natural killer (NK) cells and lymphokine-activated killer (LAK) cells have been implicated in immunosurveillance against tumor cells (Barlozzani et al. (1983) *J. Immunol.*, 131, 1024; Rayner et al. (1985) *Cancer*, 55:1327. It has been reported that the systemic administration of autologous LAK cells to patients with advanced cancer is beneficial (Mule et al. (1986) *Cancer Res.*, 46: 676). This process is tedious in that large numbers of cells are needed for each patient. Also, the treatment of cancer patients using LAK and interleakin-2 (IL-2) is accompanied by substantial toxicities (Rosenberg et al. (1987) *N. Engl. J. Med.*, 316: 889).

It has been shown that monocytes interfere with the activation of LAK activity by IL-2 (Rosenberg et al. (1987) *N. Engl. J. Med.*, 316: 889). L-Leucine methyl ester (LME) and L-phenylalanine methyl ester (PME) were shown to remove monocytes from human peripheral blood mononuclear cells (PBMC) (Thiele and Lipsky (1985) *J. Immunol.*, 134: 786; Hoyer et al. (1986) *Cancer Res.*, 46: 2834). However, LME also depleted NK activity and NK cells (Thiele and Lipsky (1985) *J. Immunol.*, 134: 786; Hoyer et al. (1986) *Cancer Res.*, 46: 2834). We have shown that depletion of monocytes by PME allows generation of LAK cells by IL-2 at cell densities of $5 \times 10^6$/mL or higher (Leung (1987) *Lymphokine Research*, 6, Abstract #1718; U.S. Pat. No. 4,849,329 to Leung and Rinehart.

It has been reported that adherent LAK (A-LAK) cells are generated by adherence to plastic of 24-hr IL-2-activated, monocyte-depleted PBMC (Melder et al. (1988) *Cancer Res.*, 48, 346). These cells are highly proliferative and cytotoxic and are enriched for LAK cells (Leu19+, LAK phenotype) and low in CD4+ (Leu3+) T lymphocytes.

In previous reports, monocytes were removed by their adherence to nylon-wool columns or by centrifugal elutriation in order to generate A-LAK cells (Melder et al. (1988) *Cancer Res.*, 48: 346). These procedures monocyte removal are tedious and complicated. Some LAK cell precursors may also adhere to the nylon-wool columns. Therefore, we have employed PME (5 mM) as a single step for monocyte depletion. We were able to generate A-LAK from PME-treated cells (copending, coassigned U.S. patent application Ser. No. 07/384,134, filed Jul. 21, 1989). Partial depletion of monocytes using lower concentrations (1 to 2.5 mM) of PME allowed more A-LAK cell expansion than did complete monocyte depletion using higher concentrations of PME.

IL-2 is a potent stimulator of NK cells and T cells. On the other hand, IL-4 was first described as a B cell growth factor (Howard et al. (1982) *J. Exp. Med.* 155: 914). IL-4 is considered as a lymphokine with multiple effects on B cells, T cells, NK cells, and monocytes (Widmer et al. (1987) *J. Exp. Med.* 166: 1447; Mitchell et al. (1989) *J. Immunol.* 142: 1548; Spits et al. (1987) *J. Immunol.* 139: 1142; Nagler et al. (1988) *J. Immunol.* 141: 2349; te Velde et al. (1989) Agents and Actions 26: 1; Spits et al. (1988) *J. Immunol.* 141: 29; Spits et al. (1988) *J. Immunol.* 141: 29; Brooks and Rees, (1988) *Clin. Exp. Immunol.* 74: 162; Kawakami et al. (1989) J. Immunol. 142: 3452). IL-4 alone cannot generate LAK activity from PBMC but can enhance specific CTL generation. IL-4 inhibited LAK induction by IL-2 but enhanced CTL induction by IL-2 (Spits et al. (1988) *J. Immunol.* 141:29; Brooks and Rees, (1988) *Clin. Exp. Immunol.* 74:162). More recently, it was reported that IL-4 enhanced cellular proliferation of IL-2-activated cells (Kawakami et al. (1989) *J. Immunol.* 142: 3452).

T lymphocytes that are positive for CD4 antigen are termed T helper/inducer cells. These CD4+ T cells are important for immunoregulation of immune functions. IL-2 is a potent stimulator of NK cells and T cells. IL-4 is considered as a lymphokine with multiple effects on B cells, T cells, NK cells, and monocytes. IL-4 enhances both CD4+ and CD8+ T cells to proliferate in response to mitogens. Therefore, the effect of IL-4 on T cells is not specific.

SUMMARY OF THE INVENTION

L-phenylalanine methyl ester (PME) depletes monocytes from peripheral blood mononuclear cells (PBMC). It allows the activation of LAK cells at high cell density by IL-2. On the other hand, IL-4 has no effect on LAK cell activation, but it inhibits the LAK cell activation by IL-2. A-LAK cells can be generated by adherence to plastic of 24-hour IL-2-activated, monocyte-depleted PBMC. These cells were highly proliferative and cytotoxic and enriched for LAK cells (Leu19+, LAK phenotype). According to the present invention, when IL-4 is present with IL- 2 during the adherence process, A-LAK cellular expansion is suppressed. Instead, a population of adherent T cells with CD4+ (Leu 3+) phenotype is expanded and enriched. The non-CD4+ cells in the population are predominantly Leu19+ NK cells and CD8+ T cells, which can also be useful in adoptive immunotherapy of cancer, AIDS, and immunologic diseases. No mitogenic and antigenic stimulation is required in the present invention.

The present invention provides a process for preparing a cell population enriched for adherent CD4+ T lymphocytes. The process comprises:

a) treating PBMC with an agent to deplete monocytes;

b) culturing the remaining cells at $5 \times 10^6$ to $1 \times 10^7$ cells/mL in culture medium containing IL-2 and IL-4, in a container to which a portion of the cells adhere;

c) removing nonadherent cells; and d) culturing the adherent cells in medium containing IL-2 and IL-4 to expand the CD4+ T cells.

This invention also features a composition comprising at least about 70% to 80% or more CD4+ T cells in a pharmaceutically acceptable carrier, and a method of treating a tumor in a mammal using the enriched CD4+ cells.

In summary, IL-2 in combination with IL-4 can be used to expand a population of adherent cells which are enriched in CD4+ phenotype. In contrast, the combination of IL-2 and IL-4 does not readily expand CD4+ cells from the nonadherent cell population.

DETAILED DESCRIPTION OF THE INVENTION.

A suspension of peripheral blood mononuclear cells (PBMC) or peripheral blood lymphocytes (PBL) is cultured for an incubation period of about 2 to 21 days at 35° to 39° C., preferably 37° C., in presence of about 4 to 7% $CO_2$. Culturing is carried out at a cell concentration in the range of about $1 \times 10^6$ to $2 \times 10^7$, preferably $5 \times 10^6$ to $1 \times 10^7$, cells per mL, in medium containing IL-2 in concentration of about 150 to 2000 pM, preferably 1000 to 2000 pM. Culturing can be performed in conventional containers, such as T-flasks, but is preferably performed in closed, gas permeable sterile bags such as SteriCell TM cell culture bags (E. I. Du Pont de Nemours & Co., Wilmington, Del.). Culturing under these conditions generates lymphokine-activated killer (LAK) cells, a population of cytolytic cells able to lyse tumor cells which are resistant to lysis by natural killer (NK) cells.

LAK cells prepared by this invention are used in adoptive immunotherapy in the manner described in U.S. Pat. No. 4,849,329 to Leung and Rinehart, issued Feb. 3, 1989, which is incorporated herein by reference.

The preferred L-amino acid is phenylalanine or tyrosine and most preferred is phenylalanine. The lower alkyl group of the ester can be methyl, ethyl, propyl, isopropyl, butyl, isobutyl or t-butyl but is preferably methyl or ethyl and is most preferably methyl. Preferred pharmaceutically acceptable salts are the hydrogen chloride and hydrogen bromide salts.

The use of PME and other lower alkyl amino acid esters in a process to prepare LAK cells is disclosed in and U.S. Pat. No. 4,849,329. Also incorporated herein by reference is U.S. patent application Ser. No. 07/313,421, filed Feb. 21, 1989.

We have previously employed PME at concentrations of about 1 to 5 mM as a single step for monocyte depletion in a process to generate A-LAK cells. The process is disclosed in coassigned U.S. patent application, Ser. No. 07/384,134, filed Jul. 21, 1989, which is incorporated herein by reference. It was discovered that it is possible to generate A-LAK from PME-treated PBMC and that treatment of PBMC with PME prior to culturing the A-LAK cells in plastic containers, results in a substantial increase in the level of expansion of the A-LAK cells, relative to the expansion in cell number obtained in the absence of PME treatment. During the expansion of the A-LAK cells, following treatment with PME, the LAK cell functional cytolytic activity remains high.

The present invention involves a novel process for the expansion and enrichment of CD4+ lymphocytes. PBMC are first treated with PME to remove monocytes and other PME-sensitive cells. The resulting lymphocytes are incubated with IL-2 and IL-4 in plastic flasks for 1 to 2 days. The adherent cells are then cultured with IL-2 and IL-4 for 8 to 21 days to obtain an increase in cell number. The cell densities used during the preparation process, including the monocyte depletion step, are preferably about $5 \times 10^6$ to $2 \times 10^7$ cells/mL, more preferably about $1 \times 10^7$ cells/mL. The adherent cells are cultured at 35° to 39° C., preferably 37° C., in presence of about 4–7% $CO_2$. The culture medium contains IL-2 in concentration of about 150 to 2000 pM, preferably 1000–2000 pM, and IL-4 in concentration of about 10 to 1000 U/mL. Culturing can be performed in conventional containers, such as T-flasks. Culturing under these conditions generates a cell population enriched for CD4+ T cells, a population of cells which is able to modulate immune responses.

In the Examples which follow, a 3-hour $^{51}$Cr-release assay was used to measure cytotoxicity of LAK cells for target tumor cells. Target tumor cells, at a concentration of about $2 \times 10^6$ to $10 \times 10^6$, were incubated with 50 $\mu$Ci of $Na^{251}CrO4$ in 0.4 mL of Tris-phosphate buffered saline for 1 hour at 37° C. The cells were washed 4 times with RPMI 1640 containing 10% fetal calf serum (FCS) and resuspended to $10^5$ cells/mL in RPMI 10% FCS. The effector cells (LAK cells) were suspended to various concentrations and 0.1 mL was added to wells in round bottom microtiter plates. The $^{51}$Cr-labeled target cells (0.1 mL) are added to all wells and the plates were centrifuged at 200 xg for 5 minutes. After 4 hours of incubation at 37° C., the plates are centrifuged again and 0.1 mL of resulting supernatant was removed from each well and counted in a gamma counter. Percent cytotoxicity was calculated from the following formula:

$$\% \text{ cytotoxicity} = \frac{\text{experimental cpm} - \text{spontaneous cpm}}{\text{total cpm} - \text{spontaneous cpm}} \times 100$$

Each variable was tested in triplicate and the resulting data expressed as % percent cytotoxicity or lysis. This cytotoxicity test is further described in *Selected Methods in Cellular Immunology*, Mishell and Shiigi, eds., 124–137, W. M. Freeman and Co., San Francisco (1980).

For cell surface marker analysis, $2 \times 10^5$ cells in 0.1 mL of chilled staining buffer solution (PBS, 15% BSA, and 0.1% sodium azide) were placed in 96-well round bottom plate. Various fluorescein-tagged antibodies were added to the cells for 30 minutes at 4° C. The cells were washed twice and resuspended in 1% paraformaldehyde prior to analysis for florescence on a flow cytometer (Becton-Dickinson, Mountain View, Calif.). Table 1 summarizes the reactivity/specificity of the antibodies used in this study.

TABLE 1

| Differentiation Antigens Identified by Monoclonal Antibodies (mAb) in this Study | | |
|---|---|---|
| CD Cluster | mAb | Cellular Reactivity/Specificity |
| CD3 | Leu4 | T cells |
| CD4 | Leu3 | Helper/inducer T cell subset |
| CD8 | Leu2 | T cell subset, NK cell subset |
| CD56 | Leu19 | NK cells, LAK cells |

EXAMPLE 1

Effect of IL-4 on A-LAK Cell Generation

PBMC were treated with 5 mM PME to deplete monocytes and cultured at $5 \times 10^6$ cells/mLi with 10 U/mL IL-2, or IL-2 and IL-4, for 20 hours in plastic flasks. Nonadherent (NA) cells were removed and the cells adherent to flasks were cultured with media containing IL-2, or IL-2 and IL-4. IL-4 (Genzyme, Boston, Mass.) was added to the adherent cells generated in media with IL-2 alone. NA cells were cultured similarly. The A-LAK cells expanded 123-fold when cultured with IL-2 alone in 14 days as shown in Table 2.

TABLE 2

Effect of IL-4 on A-LAK Cell Expansion, Cytotoxicity and Phenotype

| IL-4 (mL) | Fold Expansion | % Lysis | % Leu 2 | % Leu 3 | % Leu 4 | % Leu 19 |
|---|---|---|---|---|---|---|
| *After Adherence* | | | | | | |
| 0 | 123 | 80 | 58 | 4 | 8 | 99 |
| 10 | 146 | 78 | 57 | 3 | 5 | 99 |
| 50 | 412 | 76 | 57 | 2 | 7 | 99 |
| 200 | 547 | 82 | 50 | 2 | 4 | 99 |
| *During Adherence* | | | | | | |
| 0 | 123 | 80 | 58 | 4 | 8 | 99 |
| 10 | 46 | 69 | 49 | 21 | 27 | 76 |
| 50 | 40 | 56 | 35 | 65 | 77 | 27 |
| 200 | 30 | 43 | 30 | 77 | 88 | 17 |

PBMC were treated with 5 mM PME to deplete monocynes and cultured at $5 \times 10^6$ cells/ml with 10 U/mL IL-2 or IL-2 and IL-4 for 20 hr in plastic flasks. Nonadherent cells were removed and the cells adherent to flasks were cultured with media containing IL-2 or IL-2 and IL-4. IL-4 was added to the adherent cells generated in media with IL-2 alone. Data shown were at 14 days of culture. Cytotoxicity shown was at E:T ratio of 5:1 against 51Cr-labeled Raji target cells in a 3 hr assay.

IL-4 added after cells adhered gave four times greater cellular expansion than IL-2 alone. On the other hand, cellular expansion was suppressed by IL-4 when it was present during the adherent phase, although there was still a 30- to 46-fold cellular expansion.

A-LAK cells generated with IL-2 had 80% specific lysis of Raji target cells at an effector to target ratio of 5:1 in a 3 hour $^{51}$Cr-release assay. When IL-4 was added after the adherence phase, it had no inhibitory effect on the LAK activity. However, when IL-4 was present during the adherence phase it inhibited the LAK activity induced by IL-2 as shown in Table 2.

Phenotyping of cells grown in media containing IL-2 and IL-4 revealed that IL-4 inhibited the percent Leu19+ cells from 98% to 18% as shown in Table 2. At the same time, Leu3 and Leu4 cells were increased to 75 to 85% from about 10% in the absence of IL-4, with IL-2 alone. Therefore, IL-4 preferentially inhibited Leu19+ cellular activation and proliferation induced by IL-2, when it was present during the adherence phase of the process. It is also possible that Leu19+ cells had a negative effect on the proliferation of Leu3+ cells and inhibition of Leu19+ cells by IL-4 thus allowed the Leu3+ cells to proliferate in response to IL-2 and/or IL-4. When IL-4 was added after the adherence phase, it had no inhibitory effect on the percent Leu19+ cells as shown in Table 2.

In summary, IL-4 inhibited A-LAK generation when it was present during the adherence phase of the process and enhanced a population of cells enriched in CD4 (Leu4+). On the other hand, IL-4 enhanced the cellular expansion and the cytotoxicity of A-LAK cells when it was present after the adherence phase of the A-LAK generation process.

EXAMPLE 2

A-LAK cells were generated in the presence of IL-4 as described above. At day 8, the control A-LAK cells were 95% Leu19+ while the cells generated in the presence of IL-4 were only 65% positive as shown in (Table 3). At day 15, the IL-4 cultured cells were at only 17% positive for Leu19 and 77% positive for CD4. At day 21, the percent of cells positive for CD4 remained at 75%. In summary, an cell population enriched for CD4+ was were generated after 8 days in culture and it took about 2 weeks for optimal expansion and enrichment of CD4+ cells.

TABLE 3

Effect of IL-4 During the Adherence Phase on the Generation of Adherent CD4+ Cells and A-LAK Cells

| | | Total Cells ($\times 10^6$) | % Leu 3 (CD4) | % Leu 19 (CD56) | % Lysis E:T Ratio % | |
|---|---|---|---|---|---|---|
| | | | | | 2.5:1 | 1.25:1 |
| Day 0 | Control | 1.9 | | | | |
| | IL-4 | 1.8 | | | | |
| Day 8 | Control | 42 | 8 | 95 | 85 | 75 |
| | IL-4 | 10.8 | 34 | 65 | 29 | 15 |
| Day 15 | Control | 252 | 4 | 98 | 70 | 38 |
| | IL-4 | 150 | 77 | 17 | 29 | 16 |
| Day 21 | Control | 635 | 3 | 98 | 58 | 38 |
| | IL-4 | 240 | 75 | 14 | 18 | 8 |

Adherent cells were generated from PME-treated PBMC at $5 \times 10^5$ cells/mL in the presence of 10 U/mL IL-2, or 10 U/mL IL-2 plus 200 U/mL IL-4, for 1 day. The adherent cells were then cultured with IL-2 alone, or IL-2 and IL-4, for the various time periods.

EXAMPLE 3

Nonadherent LAK (NA-LAK) cellular expansion was somewhat enhanced by IL-4 when it was added after IL-2 activation and after the adherence of the A-LAK population as shown in Table 4. The procedure was substantially the same as in Example 1 except that NA-LAK cells were used. The LAK activity remained the same relative to the use of IL-2 alone. However, when IL-4 was present at the same time as IL-2 (during the adherence phase of the A-LAK cells), LAK activity was inhibited as shown in Table 4.

TABLE 4

Effect of IL-4 on NA-LAK Cell Expansion, Cytotoxicity and Phenotype

| IL-4 (mL) | Fold Expansion | % Lysis | % Leu 2 | % Leu 3 | % Leu 4 | % Leu 19 |
|---|---|---|---|---|---|---|
| *After Adherence* | | | | | | |
| 0 | 2.8 | 73 | 58 | 23 | 32 | 72 |
| 10 | 4.2 | 78 | 54 | 18 | 29 | 76 |
| 50 | 5.2 | 71 | 49 | 18 | 25 | 78 |
| 200 | 5.2 | 68 | 56 | 17 | 24 | 82 |
| *During Adherence* | | | | | | |
| 0 | 2.8 | 73 | 58 | 23 | 32 | 72 |
| 10 | 2.3 | 64 | 62 | 22 | 34 | 70 |
| 50 | 2.1 | 54 | 59 | 32 | 46 | 56 |
| 200 | 2.0 | 56 | 53 | 34 | 47 | 55 |

The cellular expansion was about the same with IL-2 alone compared to IL-2 plus IL-4, when IL-4 was present during the adherence step. Analysis of the surface markers of the cells showed only a slight increase in CD4+ cells when IL-4 was present during the IL-2 activation as shown in Table 4. Therefore, although the effects of IL-4 on LAK expansion or CD4+ expansion could also be observed with the NA-LAK cell cultures, the enhanced proliferation of cells was substantially reduced compared with the adherent cell (A-LAK) cultures.

What is claimed is:

1. A process for preparing a cell population enriched for adherent CD4+ T cells which process comprises:
   a) treating a peripheral blood mononuclear cell containing composition with an amount of an agent sufficient to deplete monocytes therein;

b) culturing the resultant monocyte depleted cell composition at a cell concentration ranging from $5 \times 10^6$ to $1 \times 10^7$ cells/mL in a culture medium containing IL-2 and IL-4, in a container wherein culturing in said culture medium provides for the suppression of cellular expansion of adherent lymphokine-activated killer cells and further facilitates the adherence of CD4+ T cell to the container;

c) removing the nonadherent cells and retaining said adherent cells in the container; and d) culturing said adherent cells in a culture medium containing IL-2 and IL-4 under conditions which permit the expansion of the CD4+ T cells in the container.

2. The process of claim 1 wherein the monocyte depleting agent is a lower alkyl ester of an L-amino acid or a pharmaceutically acceptable salt thereof.

3. The process of claim 2 wherein the monocyte depleting agent is L-phenylalanine methyl ester.

4. The process of claim 2 where the lower alkyl group of the ester is selected from the group consisting of methyl, ethyl, propyl, isopropyl, butyl, isobutyl and t-butyl.

5. The process of claim 2 wherein the L-amino acid is phenylalanine or tyrosine.

6. The process of claim 1 wherein culturing step b) is effected for 1 to 2 days.

7. The process of claim 1 wherein culturing step d) is effected for 8 to 21 days.

8. The process of claim 7 wherein culturing step d) is effected at 35° to 39° C. in the presence of about 4–7% $CO_2$.

9. The process of claim 1 wherein the culture medium of step d) contains an IL-2 concentration ranging from about 150 to 2000 pM and an IL-4 concentration ranging from about 10 to 100 μ/mL.

10. The process of claim 9 wherein the culture medium of step d) contains an IL-2 concentration ranging from 1000 to 2000 pM.

11. The process of claim 1 wherein the container comprises a closed, gas permeable sterile bag.

* * * * *

UNITED STATES PATENT AND TRADEMARK OFFICE
CERTIFICATE OF CORRECTION

PATENT NO. : 5,374,549
DATED : December 20, 1994
INVENTOR(S) : Kam H. LEUNG

It is certified that error appears in the above-indentified patent and that said Letters Patent is hereby corrected as shown below:

Column 1, line 26, delete "interleakin-2" and insert
-- interleukin-2 --.

Column 1, line 55, before "monocyte", insert -- for --.

Column 5, lines 16-17, delete "monocynes" and insert
-- monocytes --.

Signed and Sealed this

Thirteenth Day of June, 1995

Attest:

BRUCE LEHMAN

Attesting Officer    Commissioner of Patents and Trademarks